United States Patent
Agrawal (12)

(10) Patent No.: US 6,476,000 B1
(45) Date of Patent: Nov. 5, 2002

(54) MODULATION OF OLIGONUCLEOTIDE CPG-MEDIATED IMMUNE STIMULATION BY POSITIONAL MODIFICATION OF NUCLEOSIDES

(75) Inventor: Sudhir Agrawal, Shrewsbury, MA (US)

(73) Assignee: Hybridon, Inc., Cambridge, MA (US)

(*) Notice: Subject to any disclaimer, the term of this patent is extended or adjusted under 35 U.S.C. 154(b) by 0 days.

(21) Appl. No.: 09/639,250

(22) Filed: Aug. 14, 2000

Related U.S. Application Data

(60) Provisional application No. 60/148,798, filed on Aug. 13, 1999.

(51) Int. Cl.[7] .......................... A01N 43/04; C12Q 1/68; C12N 15/63; C07H 21/02; C07H 21/00
(52) U.S. Cl. ........................ 514/44; 435/6; 435/91.1; 435/455; 536/23.1; 536/24.5; 536/25.3
(58) Field of Search .......................... 435/6, 90, 91.1, 435/455, 375; 514/44; 536/23.1, 24.1, 24.2, 24.5, 25.3, 25.6

(56) References Cited

U.S. PATENT DOCUMENTS

| | | | | |
|---|---|---|---|---|
| 5,968,909 A | * | 10/1999 | Agrawal et al. | 514/44 |
| 6,153,595 A | * | 11/2000 | Draper et al. | 514/44 |
| 6,177,246 B1 | * | 1/2001 | Monia et al. | 435/6 |
| 6,228,642 B1 | * | 5/2001 | Baker et al. | 435/375 |
| 6,235,723 B1 | * | 5/2001 | Dean | 514/44 |

OTHER PUBLICATIONS

Sudhir Agrawal et al., Toxicologic Effects of an Oligodeoxynucleotide Phosphorothioate and Its Analogs Following Intravenous Administration in Rats, Antisense & Nucleic Acid Drug Development, 7: pp. 575–584.*

Stanley T. Crooke, Antisense Research and Application, pp. 1–50.*

Karen Pihl–Carey, Isis To Reconstruct As Crohn's Disease Drug Fails In Phase III, Bioworld Today, vol. 10, No. 239, pp. 1–2.*

Giorgio Palu'et al., In pursuit of new developments for gene therapy of human diseases, Journal of Biotechnology, 68, (1999), pp. 1–13.*

Andrea D. Branch, A good antisense molecule is hard to find, TIBS Feb. 23, 1998, pp. 45–50.*

Qiuyan Zhao et al., Effect of Different Chemically Modified Oligodeoxynucleotides on Immune Stimulation, Biochemical Pharmacology, vol. 51, pp. 173–182.*

Donald E. Macfarlane et al., Antagonism of Immunostimulatory CpG–Oligodeoxynucleotides by Quinacrine, Chloroquine, and Structurally Related Compounds, The Journal of Immunology, pp. 1122–1131.*

* cited by examiner

Primary Examiner—Sean McGarry
Assistant Examiner—Jane Zara
(74) Attorney, Agent, or Firm—Keown & Associates

(57) ABSTRACT

The invention provides methods for modulating the immune response caused by CpG-containing oligonucleotides. The methods according to the invention enables both decreasing the immunostimulatory effect for antisense applications, as well as increasing the immunostimulatory effect for immunotherapy applications.

6 Claims, 3 Drawing Sheets

MODULATION OF OLIGONUCLEOTIDE CPG-MEDIATED IMMUNE STIMULATION BY POSITIONAL MODIFICATION OF NUCLEOSIDES

CROSS REFERENCE TO RELATED APPLICATIONS

This application claims priority to provisional Patent Application Ser. No. 60/148,798, filed Aug. 13, 1999.

BACKGROUND OF THE INVENTION

1. Field of the Invention

The invention relates to the therapeutic use of oligonucleotides, both in the antisense approach, and as immunostimulatory agents.

2. Summary of the Related Art

Oligonucleotides have become indispensible tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology*, Vol 20: *Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. Agrawal and Iyer, *Curr. Op. in Biotech.* 6: 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.* 72: 209 (1972) discloses phosphodiester chemistry for oligonucleotide synthesis. Reese, *Tetrahedron Lett.* 34: 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett.* 22: 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28: 3539–3542 (1987), teaches synthesis of oligonucleotide methylphosphonates using phosphoramidite chemistry. Connolly et al., *Biochemistry* 23: 3443 (1984), discloses synthesis of oligonucleotide phosphorothioates using phosphoramidite chemistry. Jager et al.,*Biochemistry* 27: 7237 (1988), discloses synthesis of oligonucleotide phosphoramidates using phosphoramidite chemistry. Agrawal et al., *Proc. Antl. Acad. Sci. USA* 85: 7079–7083 (1988), discloses synthesis of oligonucleotide phosphoramidates and phosphorothioates using H-phosphonate chemistry.

More recently, several researchers have demonstrated the validity of the antisense approach to therapeutic treatment of disease. Crooke, Antisense Nucleic Acid Drug Dev. 8: vii–viii, discloses the successful marketing approval of a phosphorothioate oligonucleotide for the treatment of human cytomegalovirus-induced retinitis. Unfortunately, the use of phosphorothioate oligonucleotides has become more complex than originally expected. Certain effects caused by phosphorothioate oligonucleotides could not be explained by the expected antisense mechanism. For example, McIntyre et al., Antisense Res. Dev. 3: 309–322 (1993) teaches that a "sense" phosphorothioate oligonucleotide causes specific immune stimulation. This and other side effects have complicated the picture for phosphorothioate oligonucleotides. Zhaoet al., Biochemical Pharmacology 51:173–182 (1996) discloses immune stimulation mediated by two CpG-containing oligonucleotides, one complementary to the gag gene from HIV-1 (5'-CTCTCGCACCCATCTCTCTCCTTCT-3'), and the other complementary to the rev gene of HIV-1 (5'-TCGTCGCTGTCTCCGCTTCTTCTTGCC-3').

On the other hand, the observation that phosphodiester and phosphorothioate oligonucleotides can induce immune stimulation has created interest in developing this side effect as a therapeutic tool. These efforts have focussed on phosphorothioate oligonucleotides containing the dinucleotide CpG. Kuramoto et al., Jpn. J. Cancer Res. 83: 1128–1131 (1992) teaches that phosphodiester oligonucleotides containing a palindrome that includes a CpG dinucleotide can induce interferon-alpha and gamma synthesis and enhance natural killer activity. Krieg et al., Nature 371: 546–549 (1995) discloses that phosphorothioate CpG-containing oligonucleotides are immunostimulatory. Liang et al., J. Clin. Invest. 98: 1119–1129 (1996) discloses that such oligonucleotides activate human B cells. Moldoveanu et al., Vaccine 16: 1216–124 (1998) teaches that CpG-containing phosphorothioate oligonucleotides enhance immune response against influenza virus. McCluskie and Davis, The Journal of Immunology 161: 4463–4466 (1998) teaches that CpG-containing oligonucleotides act as potent immunostimulatory agents, enhancing immune response against hepatitis B surface antigen. Agrawal, U.S. Pat. No. 5,968,909, teaches that backbone modification of C or G suppresses this effect.

These reports make clear that there is a need to be able to modulate the immune response caused by CpG-containing oligonucleotides. Ideally, such modulation should include decreasing the immunostimulatory effect for antisense applications, as well as increasing the immunostimulatory effect for immunotherapy applications.

BRIEF SUMMARY OF THE INVENTION

The invention provides methods for modulating the immune response caused by CpG-containing oligonucleotides. The methods according to the invention enable both decreasing the immunostimulatory effect for antisense applications, as well as increasing the immunostimulatory effect for immunotherapy applications. Thus, the invention further provides oligonucleotides having optimal levels of immunostimulatory effect for either application and methods for using such oligonucleotides.

The present inventor has surprisingly discovered that positional modification of CpG-containing oligonucleotides dramatically affects their immunostimulatory capabilities. In particular, 2' alkylation or alkoxylation of oligonucleotides at particular positions 5' or 3' to the CpG dinucleotide either enhances or reduces their immunostimulatory effect.

In a first aspect, the invention provides a method for reducing the immunostimulatory effect of a CpG-containing oligonucleotide. The method according to this aspect of the invention comprises introducing a 2' substituted nucleoside into the oligonucleotide at a position adjacent to, and on the 5' side of the CpG dinucleotide, wherein at least one nucleoside is not a 2'-O-methylribonucleoside and the oligonucleotide is not complementary to the gag or rev gene of human immunodeficiency virus type 1.

In a second aspect, the invention provides a CpG-containing oligonucleotide having a reduced immunostimulatory effect, wherein the oligonucleotide comprises a 2' substituted nucleoside at a position adjacent to, and on the 5' side of the CpG dinucleotide, wherein at least one nucleoside is not a 2'-O-methylribonucleoside and the oligonucleotide is not complementary to the gag or rev gene of human immunodeficiency virus type 1.

In a third aspect, the invention provides a method for obtaining an antisense-specific reduction in the expression of a gene in a mammal, the method comprising administering to the mammal a CpG-containing oligonucleotide having a reduced immunostimulatory effect, wherein the oligonucleotide comprises a 2' substituted nucleoside at a position adjacent to, and on the 5' side of the CpG dinucleotide, wherein at least one nucleoside is not a 2'-O-methylribonucleoside and the oligonucleotide is not complementary to the gag or rev gene of human immunodeficiency virus type 1.

In a fourth aspect, the invention provides a method for increasing the immunostimulatory effect of a CpG-containing oligonucleotide, wherein the oligonucleotide is not an antisense oligonucleotide complementary to Ha-ras or the gag or rev gene of human immunodeficiency virus type 1. The method according to this aspect of the invention comprises introducing into the oligonucleotide a 2' substituted nucleoside at a position selected from the group consisting of second nucleoside 5' to the CpG dinucleotide, third nucleoside 5' to the CpG dinucleotide, fourth nucleoside 5' to the CpG dinucleotide, fifth nucleoside 5' to the CpG dinucleotide, sixth nucleoside 5' to the CpG dinucleotide, first nucleoside 3' to the CpG dinucleotide, second nucleoside 3' to the CpG dinucleotide, third nucleoside 3' to the CpG dinucleotide, fourth nucleoside 3' to the CpG dinucleotide, fifth nucleoside 3' to the CpG dinucleotide, sixth nucleoside 3' to the CpG dinucleotide, and combinations thereof. In certain preferred embodiments, the oligonucleotide is not an antisense oligonucleotide. In alternative embodiments the oligonucleotide may be an antisense oligonucleotide.

In a fifth aspect, the invention provides CpG-containing oligonucleotides having increased immunostimulatory effects, the oligonucleotide comprising a 2' substituted nucleoside at a position selected from the group consisting of second nucleoside 5' to the CpG dinucleotide, third nucleoside 5' to the CpG dinucleotide, fourth nucleoside 5' to the CpG dinucleotide, fifth nucleoside 5' to the CpG dinucleotide, sixth nucleoside 5' to the CpG dinucleotide, first nucleoside 3' to the CpG dinucleotide, second nucleoside 3' to the CpG dinucleotide, third nucleoside 3' to the CpG dinucleotide, fourth nucleoside 3' to the CpG dinucleotide, fifth nucleoside 3' to the CpG dinucleotide, sixth nucleoside 3' to the CpG dinucleotide, and combinations thereof, wherein the oligonucleotide is not an antisense oligonucleotide complementary to Ha-ras or the gag or rev gene of human immunodeficiency virus type 1. In certain preferred embodiments, the oligonucleotide is not an antisense oligonucleotide.

In a sixth aspect, the invention provides a method for inducing an immune response in a mammal, the method comprising administering to the mammal an oligonucleotide comprising a 2' substituted nucleoside at a position selected from the group consisting of second nucleoside 5' to the CpG dinucleotide, third nucleoside 5' to the CpG dinucleotide, fourth nucleoside 5' to the CpG dinucleotide, fifth nucleoside 5' to the CpG dinucleotide, sixth nucleoside 5' to the CpG dinucleotide, first nucleoside 3' to the CpG dinucleotide, second nucleoside 3' to the CpG dinucleotide, third nucleoside 3' to the CpG dinucleotide, fourth nucleoside 3' to the CpG dinucleotide, fifth nucleoside 3' to the CpG dinucleotide, sixth nucleoside 3' to the CpG dinucleotide, and combinations thereof, wherein the oligonucleotide is not an antisense oligonucleotide complementary to Ha-ras or the rev or gag gene of human immunodeficiency virus type 1. In certain preferred embodiments, the oligonucleotide is not an antisense oligonucleotide.

DETAILED DESCRIPTION OF THE PREFERRED EMBODIMENTS

Figure 1:
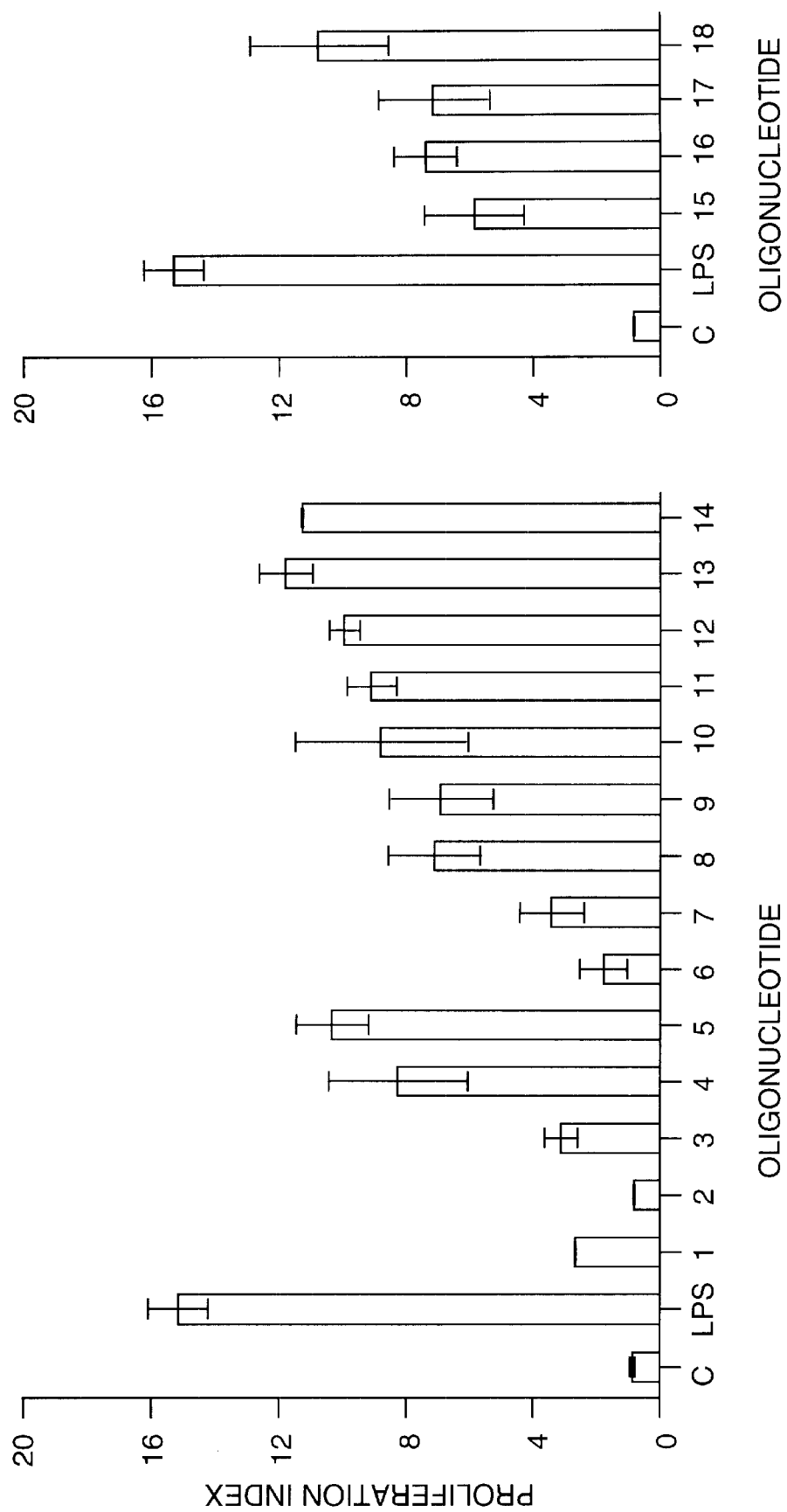
FIG. 1 shows results of a proliferation assay of mouse spleen cells in the presence of no oligonucleotide (C), lipopolysaccharide (LPS), or various oligonucleotides.

The invention relates to the therapeutic use of oligonucleotides, both in the antisense approach, and as immunostimulatory agents. The patents and publications cited herein reflect the level of knowledge in the field and are hereby incorporated by reference in their entirety. In the event of conflict between any teaching of any reference cited herein and the present specification, the latter shall prevail, for purposes of the invention.

The invention provides methods for modulating the immune response caused by CpG-containing oligonucleotides. The methods according to the invention enable both decreasing or increasing the immunostimulatory effect for antisense applications, as well as increasing the immunostimulatory effect for immunotherapy applications. Thus, the invention further provides oligonucleotides having optimal levels of immunostimulatory effect for either application and methods for using such oligonucleotides.

The present inventor has surprisingly discovered that positional modification of CpG-containing oligonucleotides dramatically affects their immunostimulatory capabilities. In particular, 2' substitution, including without limitation alkylation or alkoxylation of oligonucleotides at particular positions 5' or 3' to the CpG dinucleotide either enhances or reduces their immunostimulatory effect.

In a first aspect, the invention provides a method for reducing the immunostimulatory effect of a CpG-containing oligonucleotide. The method according to this aspect of the invention comprises introducing a 2' substituted nucleoside into the oligonucleotide at a position adjacent to, and on the 5' side of the CpG dinucleotide, wherein at least one nucleoside is not a 2'-O-methylribonucleoside and the oligonucleotide is not complementary to the gag or rev gene of human immunodeficiency virus type 1. In preferred embodiments the method is used to make an oligonucleotide that is complementary to a gene or gene transcript. In certain preferred embodiments, the oligonucleotide has antisense activity. In some preferred embodiments, only one 2' substituted nucleoside is introduced into the oligonucleotide for each CpG dinucleotide present in the oligonucleotide. In some preferred embodiments, only one 2' substituted nucleoside is introduced into the oligonucleotide.

As used for the first three aspects of the invention, the term "complementary" means having the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such hybridization can be inferred from the observation of specific gene expression inhibition.

As used for the first three aspects of this invention, "antisense activity" means that the oligonucleotide, when introduced into a cell or an animal, causes a reduction in the expression of the RNA to which it is complementary.

The method according to this aspect of the invention can be conveniently carried out using any of the well-known synthesis techniques by simply using the appropriate 2' substituted monomer synthon in the synthesis process in the cycle immediately following the incorporation of the CpG dinucleotide. Preferred monomers include phosphoramidites, phosphotriesters and H-phosphonates. Thus, for purposes of the invention, "introducing a 2' substituted nucleoside into the oligonucleotide at a position adjacent to, and on the 5' side of the CpG dinucleotide" simply means synthesizing an oligonucleotide that has a 2' substituted nucleoside at such a position.

In a second aspect, the invention provides a CpG-containing oligonucleotide having a reduced immunostimulatory effect, wherein the oligonucleotide comprises a 2' substituted nucleoside at a position adjacent to, and on the 5' side of the CpG dinucleotide, wherein at least one nucleoside is not a 2'-O-methylribonucleoside and the oligonucleotide is not complementary to the gag or rev gene of human immunodeficiency virus type 1. Preferably, such oligonucleotides will have from about 12 to about 50 nucleotides, most preferably from about 12 to about 35 nucleotides. Preferred oligonucleotides according to this aspect of the invention are complementary to a gene or gene transcript. More preferably, such oligonucleotides have antisense activity. In some preferred embodiments, the oligonucleotide has only one 2' substituted nucleoside for each CpG dinucleotide present in the oligonucleotide. In some preferred embodiments, the oligonucleotide has only one 2' substituted nucleoside.

In a third aspect, the invention provides a method for obtaining an antisense-specific reduction in the expression of a gene in a mammal, the method comprising administering to the mammal a CpG-containing oligonucleotide having a reduced immunostimulatory effect, wherein the oligonucleotide comprises a 2' substituted nucleoside at a position adjacent to, and on the 5' side of the CpG dinucleotide, wherein at least one nucleoside is not a 2'-O-methylribonucleoside and the oligonucleotide is not complementary to the gag or rev gene of human immunodeficiency virus type 1. In some preferred embodiments, the oligonucleotide has only one 2' substituted nucleoside for each CpG dinucleotide present in the oligonucleotide. In some preferred embodiments, the oligonucleotide has only one 2' substituted nucleoside.

In the methods according to this aspect of the invention, preferably, administration of oligonucleotides should be parenteral, oral, sublingual, transdermal, topical, intranasal, intravaginal, respiratory, intravitreal, or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.01 mg oligonucleotide per patient per day to about 200 mg oligonucleotide per kg body weight per day. The oligonucleotide may be formulated or naked. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

The method according to this aspect of the invention is useful in animal models of disease or gene expression, and is further useful for the therapeutic treatment of human disease.

In a fourth aspect, the invention provides a method for increasing the immunostimulatory effect of an immunostimulatory motif (e.g. CpG)-containing oligonucleotide, wherein the oligonucleotide is not an antisense oligonucleotide complementary to Ha-ras or the gag or rev gene of human immunodeficiency virus type 1. The method according to this aspect of the invention comprises introducing into the oligonucleotide a 2' substituted nucleoside at a position selected from the group consisting of second nucleoside 5' to the CpG dinucleotide, third nucleoside 5' to the CpG dinucleotide, fourth nucleoside 5' to the CpG dinucleotide, fifth nucleoside 5' to the CpG dinucleotide, sixth nucleoside 5' to the CpG dinucleotide, first nucleoside 3' to the CpG dinucleotide, second nucleoside 3' to the CpG dinucleotide, third nucleoside 3' to the CpG dinucleotide, fourth nucleoside 3' to the CpG dinucleotide, fifth nucleoside 3' to the CpG dinucleotide, sixth nucleoside 3' to the CpG dinucleotide, and combinations thereof. In certain preferred embodiments, the oligonucleotide is not an antisense oligonucleotide.

The method according to this aspect of the invention can be conveniently carried out using any of the well-known synthesis techniques by simply using the appropriate 2' substituted monomer synthon in the synthesis process in the cycle immediately following the incorporation of the CpG dinucleotide. Preferred monomers include phosphoramidites, phosphotriesters and H-phosphonates. Thus, for purposes of the invention, "introducing into the oligonucleotide a 2' substituted nucleoside at a position selected from the group consisting of second nucleoside 5' to the CpG dinucleotide, third nucleoside 5' to the CpG dinucleotide, fourth nucleoside 5' to the CpG dinucleotide, fifth nucleoside 5' to the CpG dinucleotide, sixth nucleoside 5' to the CpG dinucleotide, first nucleoside 3' to the CpG dinucleotide, second nucleoside 3' to the CpG dinucleotide, third nucleoside 3' to the CpG dinucleotide, fourth nucleoside 3' to the CpG dinucleotide, fifth nucleoside 3' to the CpG dinucleotide, sixth nucleoside 3' to the CpG dinucleotide, and combinations thereof" simply means synthesizing an oligonucleotide that has a 2' substituted nucleoside at such a position or positions.

For purposes of the fourth, fifth and sixth aspects of the invention, an "antisense oligonucleotide" is an oligonucleotide that is exactly complementary to a gene or gene transcript, and capable of reducing the expression of the gene or gene transcript to which it is exactly complementary.

In a fifth aspect, the invention provides immunostimulatory motif (e.g. CpG) containing oligonucleotides having increased immunostimulatory effects, the oligonucleotide comprising a 2' substituted nucleoside at a position selected from the group consisting of second nucleoside 5' to the CpG dinucleotide, third nucleoside 5' to the CpG dinucleotide, fourth nucleoside 5' to the CpG dinucleotide, fifth nucleoside 5' to the CpG dinucleotide, sixth nucleoside 5' to the CpG dinucleotide, first nucleoside 3' to the CpG dinucleotide, second nucleoside 3' to the CpG dinucleotide, third nucleoside 3' to the CpG dinucleotide, fourth nucleoside 3' to the CpG dinucleotide, fifth nucleoside 3' to the CpG dinucleotide, sixth nucleoside 3' to the CpG dinucleotide, and combinations thereof, wherein the oligonucleotide is not an antisense oligonucleotide complementary to Ha-ras or the gag or rev gene of human immunodeficiency virus type 1. In certain preferred embodiments, the oligonucleotide is not and antisense oligonucleotide. Preferred oligonucleotides according to the fourth, fifth and sixth aspects of the invention are from about 6 to about 50 nucleotides in length, and may further comprise modified internucleotide linkages or modified sugars to improve stability.

In a sixth aspect, the invention provides a method for inducing an immune response in a mammal, the method comprising administering to the mammal an immunostimulatory motif (e.g. CpG)-containing oligonucleotide comprising 2' substituted nucleoside at a position selected from the group consisting of a second nucleoside 5' to the CpG dinucleotide, third nucleotide 5' to the CpG dinucleotide, fourth nucleoside 5' to the CpG dinucleotide, fifth nucleoside 5' to the CpG dinucleotide, sixth nucleoside 5' to the CpG dinucleotide, first nucleoside 3' to the CpG dinucleotide, second nucleoside 3' to the CpG dinucleotide, third nucleoside 3' to the CpG dinucleotide, fourth nucleoside 3' to the CpG dinucleotide, fifth nucleoside 3' to the CpG dinucleotide, sixth nucleoside 3' to the CpG dinucleotide, and combinations therof, wherein the oligonucleotide is not and antisense oligonucleotide complementary to Ha-ras or the rev or gag gene of human immunodeficiency virus type 1. In certain preferred embodiments of the is aspect of the invention, the oligonucleotide is not and antisense oligonucleotide.

In the methods according to this aspect of the invention, preferably, administration of oligonucleotides should be parenteral, oral, sublingual, transdermal, topical, intranasal, intravitreal, or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.01 mg oligonucleotide per patient per day to about 200 mg oligonucleotide per kg body weight per day. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of IL-12 induction, and immune cell mitogenesis. The oligonucleotides may be administered alone, or in combination with specific antigens, which may or may not be physically attached to the oligonucleotide. Such administration may optionally include the use of adjuvants.

The method according to this aspect of the invention is useful for model studies of the immune system, and is further useful for the therapeutic treatment of human disease.

Figure 3:
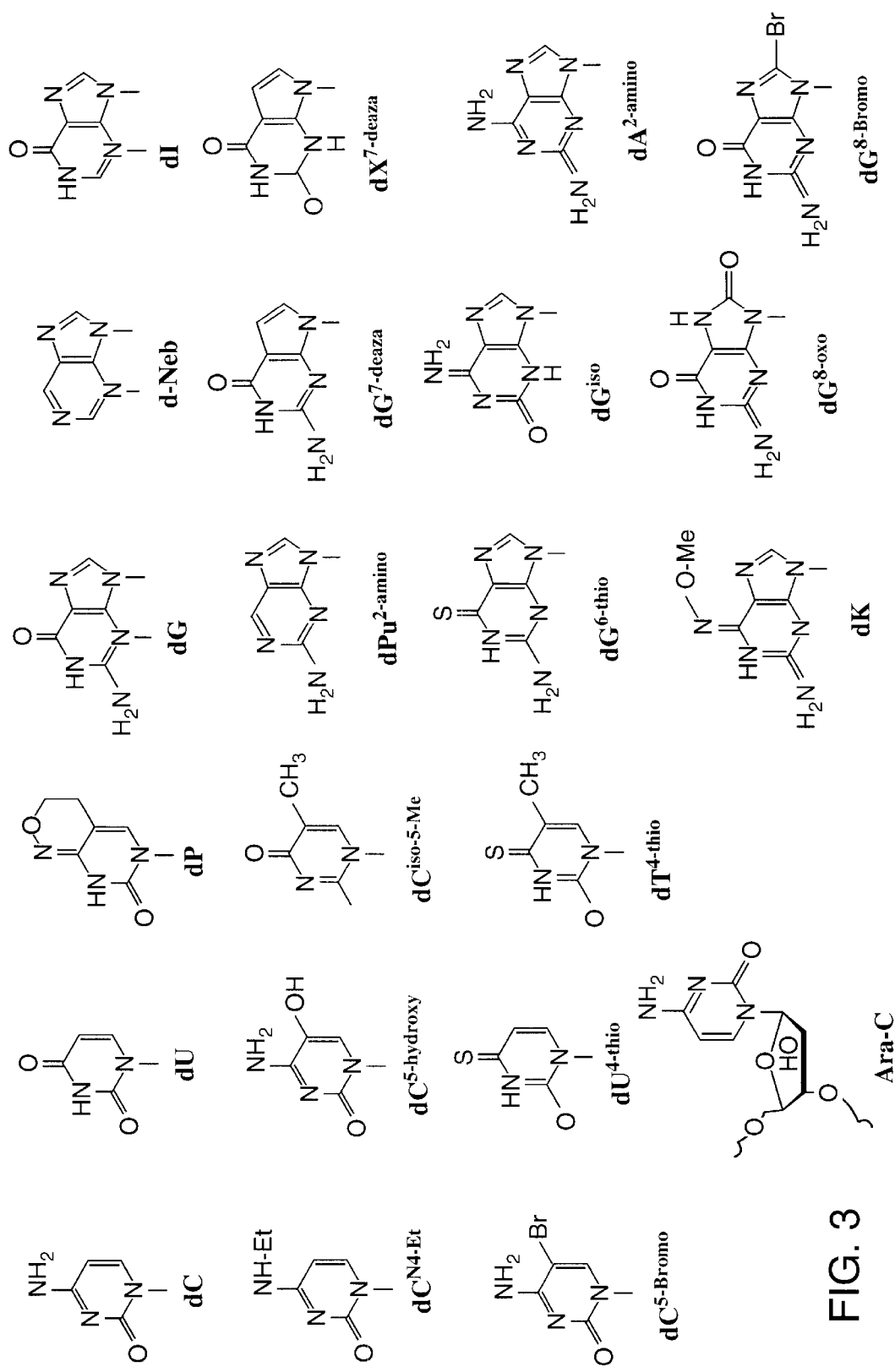
FIG. 3 shows preferred embodiments of modified bases.

For purposes of all aspects of the invention, the term "oligonucleotide" includes polymers of two or more deoxyribonucleotide, or any modified nucleoside, including 2' substituted nucleosides, ribonucleosides, deazanucleosides or any combination thereof. Such monomers may be coupled to each other by any of the numerous known internucleoside linkages. In certain preferred embodiments, these internucleoside linkages may be nonionic, boronic, phosphodiester, phosphotriester, phosphorothioate, or phosphoramidate linkages, 2'-5', 3'-5', 3'-3' linkages of any of the foregoing, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2' substituted" means substitution of the 2' position of the pentose moiety with a halogen (preferably Cl, Br, or F), or an —O-lower alkyl group containing 1–6 saturated or unsaturated carbon atoms, or with an —O-aryl or —O-allyl group having 2–6 carbon atoms, wherein such alkyl,aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino group or a halo group, but not with a 2'-H group. Such oligonucleotides include oligonucleotides having modified sugars (e.g. arabinose, hexose) and other backbone modifications, e.g., as in peptide nucleic acid and locked nucleic acid. Such oligonucleotides may also have naturally occurring bases or modified heterocyclic rings, including without limitation those shown in FIG. 3. For purposes of all aspects of the invention, the terms "CpG" or "CpG dinucleotide" means the dinucleotide 5'-cytidine-guanosine-3', wherein p is an internucleotide linkage, and wherein the sugar backbone of the dinucleotide is deoxyribose, modified sugar, or combinations thereof. In preferred embodiments of the first three aspects of the invention, p is selected from phosphodiester, phosphorothioate, phosphorodithioate, stereospecific (Rp or Sp) phosphorothioate covalent linkages of any of the above. The non-phosphodiester, non-phosphorothioate embodiments will further reduce immunostimulatory effects. In preferred embodiments of the last three aspects of the invention, p is selected from phosphodiester, phosphorothioate and phosphordithioate.

The following examples are intended to further illustrate certain preferred embodiments of the invention, and are not intended to limit the scope of the invention.

EXAMPLE 1

Modulation of Immulostimulatory Effect In Vitro

To study the impact of site of chemical modification of PS-oligos containing CpG motif, we chose two oligonucleotides. Oligo 1, which contains one CpG motif, and Oligo 15, which contains two CpG motifs. Both of these oligos have been studied earlier and have shown to be immunostimulatory. To evaluate the immunostimulatory activity of oligonucleotides in the present study, we have used mouse spleen cell proliferation assay.

TABLE 1

Oligodeoxynucleotide Phosphorothioates and Site of Modifications

| Oligo No. | Sequence & Modification (5'–3') |
|---|---|
| 1 | TCCATGACGTTCCTGATGC |
| 2 | TCCATGACGTTCCTGATGC |
| 3 | TCCAUGACGTTCCTGATGC |
| 4 | TCCAUGACGTTCCTGATGC |
| 5 | TCCATGACGTTCCTGATGC |
| 6 | TCCATGACGUUCCTGATGC |
| 7 | TCCATGACGTUCCTGATGC |
| 8 | TCCATGACGTTCCTGATGC |
| 9 | TCCATGACGTTCCUGATGC |
| 10 | TCCATGACGTTCCUGATGC |
| 11 | TCCATGACGTTCCTGATGC |
| 12 | TCCATGACGTTCCUGATGC |
| 13 | TCCATGACGTTCCTGAUGC |
| 14 | TCCATGACGTTCCTGAUGC |
| 15 | TCCATGACGTTCCTGACGTT |
| 16 | TCCAUGACGTTCCTGACGTT |
| 17 | TCCATGACGTTCCCUGACGTT |
| 18 | TCCAUGACGTTCCCUGACGTT |

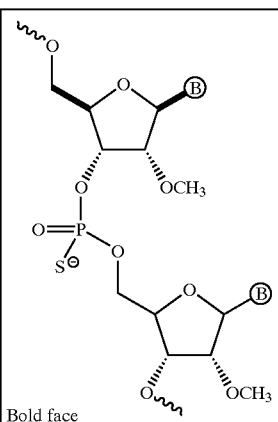

Bold face / Normal face

Mouse spleen lymphocytes were cultured with oligonucleotides at concentration of 0.1, 1, and 10 μg/mL. Oligo 1 induced a dose dependent effect on cell proliferation. At 0.1 μg/mL, the proliferation index was 2.87 (FIG. 1).

Substitution of 5'-flanking GA deoxynucleosides of CpG motif of Oligo 1 with 2'-OMe, (oligo 2), resulted in complete suppression of cell proliferation at all concentrations used (FIG. 1). At 0.1 μg/mL, cell proliferation index was similar to medium alone. Substitution of the 3'- flanking TT deoxynucleosides of CpG A motif of Oligo 1 with 2'-OMe (Oligo 6) did not have such an impact on cell proliferation. The proliferation index with Oligo 6 was 2.07 (FIG. 1). To further understand if substitution of two deoxynucleosides in the 5'-flanking region with 2'-OMe away from the CpG motif would have any impact on induced cell proliferation, we synthesized oligos 3,4 and 5 (Table 1). Two deoxynucleosides were substituted with 2'-OMe, leaving one, two and three deoxynucleosides respectively in between the site of substitution and the CpG motif. The proliferation index of oligo 3,4, and 5 was 3.42, 8.44, and 10.38 respectively which is an increase of 29, 297 and 400 percent, respectively, compared to oligo 1 (FIG.1). Substitution of remaining deoxynucleosides further towards 5'-end than in oligo 5 showed no further increase in proliferation index (data not shown).

Similar substitutions were made in oligo 1 in the 3'-flanking region to CpG motif. Oligo 7, 8, 9, 10 and 11 were synthesized in which two deoxynucleosides were substituted with 2'-OMe leaving one, two, three, four and five deoxynucleosides respectively in between CpG motif and 2'-OMe substitution. The proliferation index of oligo 7, 8, 9, 10 and 11 were 3.63, 7.22, 7.01, 8.85, and 9.24 respectively. Compared to oligo 1, the increase in proliferation index for oligo 7, 8, 9, 10 and 11 was 39, 231, 221, 317 and 338 percent respectively.

From these results, it is evident that substitution of two deoxynucleotides at either the 5'-end or the 3'-end of the CpG motif (e.g. Oligo 5 or 9) increases the immunostimulatory activity. It is possible that the substitution made in Oligo 5 and Oligo 9 will have additive effects in further increasing the immunostimulatory activity. We synthesized Oligo 12, which had two deoxynucleosides that were substituted with 2'-OMe at both the 3'-end and the 5'-end. Oligo 12 did not show further increase in the proliferation index when compared with Oligo 5; however, it had increased proliferation index compared to Oligo 9.

To explore if the above observations made with the use of Oligos 3 to 5 and Oligos 7 to 11 are sequence specific or general, we made the same modifications to Oligo 15, which contains two CpG motifs. Oligo 15 had a proliferation index of 5.83 at a concentration of 0.1 μg/mL. Substitution of two deoxynucleosides at 5'-ends of individual CpG motifs leaving two deoxynucleosides in between CpG motif and substitution with 2'-OMe, oligo 16 and 17, showed proliferation index of 7.34 and 7.13 respectively, which is only an increase of twenty percent compared to oligo 15. Substitution of two deoxynucleosides in the 5'- flanking region of both CpG motifs (Oligo 18) showed a higher proliferation index 10.62, which is an increase of about fifty percent compared to Oligo 15.

EXAMPLE 2

Effect of Nuclease Stability on Immunostimulatory Activity

In addition to site specific substitution, we also questioned if increased metabolic stability of PS-oligo containing CpG motif may result in increased cell proliferation and if that can be combined with 5'-substitutions to further increase the cell proliferation activity. Oligo 13 was synthesized in which four continuous deoxynucleosides at the 3'- end of oligo 1 were substituted with 2'-OMe, which results in a significant increase in stability towards nucleases. Oligo 13 had a proliferation index of 11.92, which is an increase of about 480% compared to oligo 1 (FIG. 1). Further modification of oligo 13 by substitution of two deoxynucleosides at 5'-end (oligo 14) did not result in further increase in proliferation index.

Figure 2:
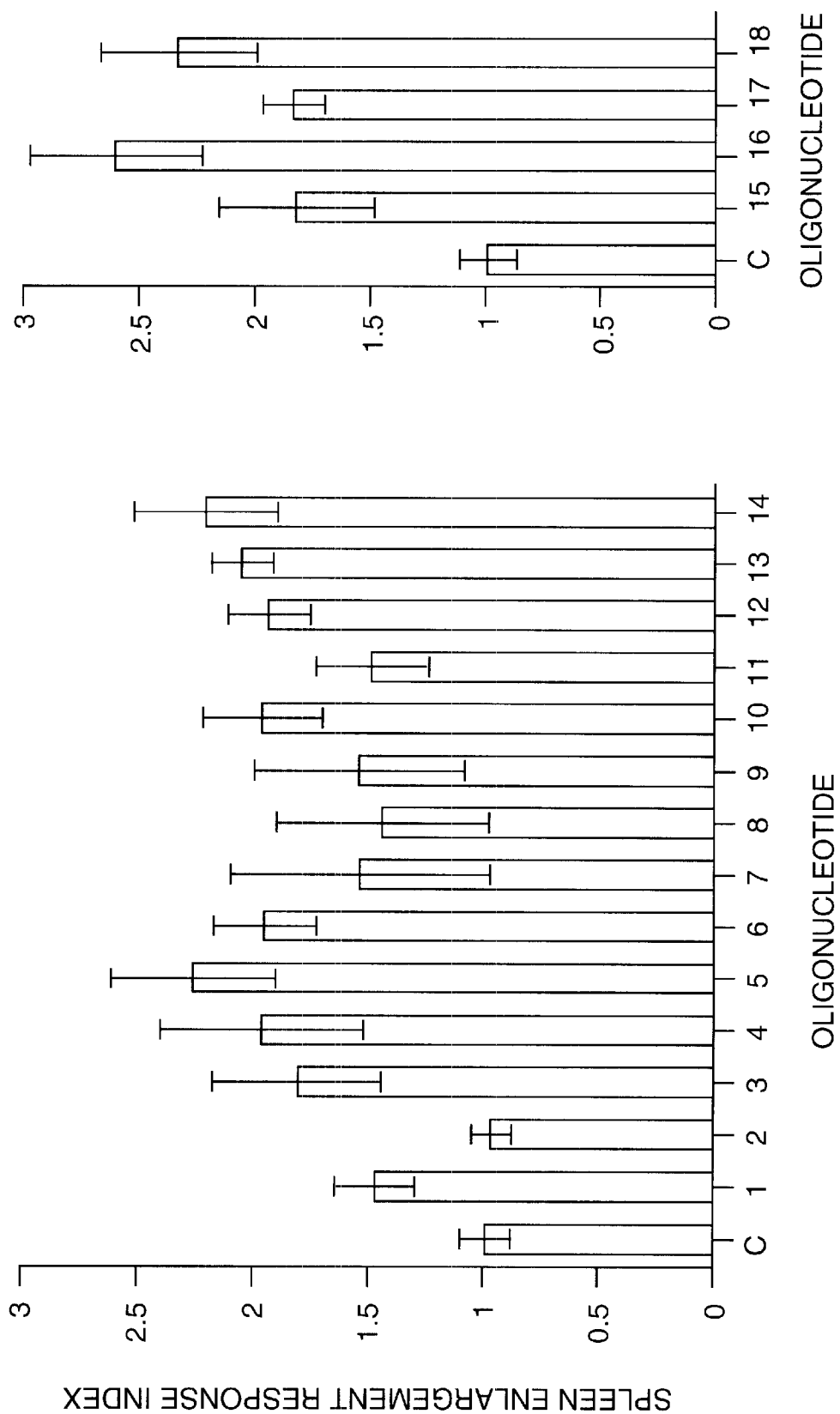
FIG. 2 shows spleen enlargement in mice administered no oligonucleotide or various oligonucleotides.

After observing that above substitutions in PS-oligos modulates its immunostimulatory activity based on cell culture assay, we administered oligonucleotides listed in Table 1 intraperitonealy to mice and measured the spleen weights to confirm that if substitutions have same effect in vivo. Administration of oligo 1 caused about 50 percent increase in spleen weight (FIG. 2). Oligo 2, which had shown no immunostimulatory activity in cell culture assay, showed no increase in spleen weights (FIG. 2). Substitution of two deoxynucleotides away from CpG motif towards 5'-end, oligo 3, 4, and 5 showed progressive increase in spleen weights which were 67, 95 and 157 percent respectively more compared to mice treated with oligo 1 (FIG. 2), confirming an increase in their immunostimulatory activity. Substitutions of two deoxynucleosides with 2'-OMe toward the 3'-end of the CpG motif, in general, had less significant increase in spleen weight. Only oligo 6 and 11 caused an increase in spleen weight of 97 and 95 percent compared to oligo 1. Oligo 12, which had substitutions made at both the 3'-end and the 5'-end showed 95 percent increase in spleen weight compared to oligo 1 (FIG. 2).

Oligos 15, 16, 17, and 18, all of which contain two CpG motifs, showed increase in spleen weight following administration of a dose of 5 mg/kg. Oligo 15 caused 175 percent increase of spleen weight compared to untreated mice. Oligo 16, in which two of the 5'-end CpG motifs were substituted with 2'-OMe, caused a 93 percent increase in spleen weight compared to oligo 15 (FIG. 2). Oligo 17, which has substitutions at the 5'-end of one CpG (but at the 3'-end of the other CpG motif showed no further increase in spleen weight. Substitution at the 5'-end of both CpG motifs did not result in further increases in spleen weight compared to oligo 16, however had only about 60 percent increase over oligo 15 (FIG. 2).

Oligo 13, which is metabolically stable compared to oligo 1, showed 114 percent increase in spleen weight compared to Oligo 1, and was in agreement with cell proliferation data. Similar results were observed with Oligo 14, which has increased metabolic stability and substituted at the 5'-end of CpG motif (FIG. 2).

What is claimed is:

1. A method for reducing the immunostimulatory effect of a CpG-containing oligonucleotide, the method comprising introducing a 2'-substituted nucleoside into the oligonucleotide at a position adjacent to, and on the 5'side of the CpG dinucleoside, wherein at least one nucleoside is a deoxyribonucleoside, and the oligonucleotide is not complementary to the gag or rev gene of human immunodeficiency type 1, wherein only one 2' substituted nucleoside is introduced into the oligonucleotide for each CpG dinucleotide present in the oligonucleotide, thereby producing an oligonucleotide having a reduced immunostimulatory effect relative to a CpG-containing oligonucleotide that does not comprise a 2'-substituted nucleoside at a position adjacent to, and on the 5' side of the CpG dinucleoside.

2. The method according to claims 1, wherein only one 2'-substituted nucleoside is introduced into the oligonucleotide.

3. A CpG-containing oligonucleotide having a reduced immunostimulatory effect, wherein the oligonucleotide comprises a 2'-substituted nucleoside at a position adjacent to, and on the 5' side of the CpG dinucleoside, wherein at least one nucleoside is a deoxyribonucleoside and the oligonucleotide is not complementary to the gag or rev gene of human immunodeficiency type 1, wherein the oligonucleotide has only one 2' substituted nucleoside for each CpG dinucleotide present in the oligonucleotide, and wherein the oligonucleotide has a reduced immunostimulatory effect relative to a CpG-containing oligonucleotide that does not comprise a 2'-substituted nucleoside at a position adjacent to, and on the 5' side of the CpG dinucleoside.

4. The oligonucleotide according to claim 3, wherein the oligonucleotide has only one 2' substituted nucleoside for each CpG dinucleotide present in the oligonucleotide.

5. A method for obtaining an antisense-specific reduction in the expression of a gene in a mammal, the method comprising administering to the mammal a CpG-containing oligonucleotide having a reduced immunostimulatory effect, wherein the oligonucleotide comprises a 2'-substituted nucleoside at a position adjacent to, and on the 5' side of the CpG dinucleoside, wherein at least one nucleoside is a deoxyribonucleoside, and the oligonucleotide is not complementary to the gag or rev gene of human immunodeficiency type 1, wherein the oligonucleotide has only one 2' substituted nucleoside for each CpG dinucleotide present in the oligonucleotide, and wherein the oligonucleotide has a reduced immunostimulatory effect relative to a CpG-containing oligonucleotide that does not comprise a 2'-substituted nucleoside at a position adjacent to, and on the 5' side of the CpG dinucleoside.

6. The method according to claim 5, wherein the oligonucleotide has only one 2' substituted nucleoside for each CpG dinucleotide present in the oligonucleotide.

* * * * *